United States Patent [19]

Hughes et al.

[11] Patent Number: 5,138,051

[45] Date of Patent: Aug. 11, 1992

[54] RAPAMYCIN ANALOGS AS IMMUNOSUPPRESSANTS AND ANTIFUNGALS

[75] Inventors: Philip F. Hughes, Chapel Hill, N.C.; John H. Musser, Alameda, Calif.

[73] Assignee: American Home Products Corporation, New York, N.Y.

[21] Appl. No.: 741,714

[22] Filed: Aug. 7, 1991

[51] Int. Cl.⁵ ............................................. C07D 491/06
[52] U.S. Cl. ..................................................... 540/456
[58] Field of Search ........................ 540/456; 514/183

[56] References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 4,316,885 | 2/1982 | Rakhit | 540/456 |
| 4,401,653 | 4/1983 | Eng | 540/456 |
| 4,650,803 | 3/1987 | Stella et al. | 540/456 |
| 4,885,171 | 12/1989 | Sehgal et al. | 540/456 |

FOREIGN PATENT DOCUMENTS 0401747 12/1990 European Pat. Off. ............ 540/456

OTHER PUBLICATIONS

J. Antibiot. 28,721–726, (1975).
J. Antibiot, 28, 727–732 (1975).
J. Antibot, 31, 539–545 (1978).
Can. J. Phsiol. Pharmacol. 55, 48 (1977).
FASEB 3,3411 (1989).
FASEB 3,5256 (1989).
Lancet, 1183, (1978).

*Primary Examiner*—Robert T. Bond
*Attorney, Agent, or Firm*—Robert F. Boswell, Jr.

[57] ABSTRACT

Reduction of C-33 ketone of rapamycin gives the C-33 hydroxy analog of Formula I.

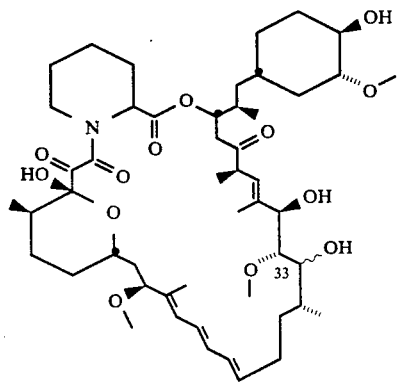

Formula I

The reduction product prevents cleavage of the C-31/C-32 bond due to base degradation. The Formula I compounds exhibit immunosuppressant, antifungal, and antiinflammatory activities.

2 Claims, No Drawings

RAPAMYCIN ANALOGS AS IMMUNOSUPPRESSANTS AND ANTIFUNGALS

BACKGROUND OF THE INVENTION

This invention relates to compounds of Formula I where the ketone functionality at position 33 is rapamycin is replaced with a hydroxy group and which are useful in the treatment of transplantation rejection, autoimmune diseases (i.e. lupus, rheumatoid arthritis, diabetes mellitus, multiple sclerosis), *Candida albicans* infections, and diseases of inflammation. More particularly, this invention is concerned with the isomer where the hydroxy group at position 33 is in the α- position and the product thus has the R configuration at C-33.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibot. 28, 721 (1975); S. N. Seghal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Caine et al., Lancet 1183 (1978)].

Mono- and diacylated derivatives of rapamycin (esterified at the 28 and 43 positions) have been shown to be useful as antifungal agents (U.S. pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

SUMMARY OF THE INVENTION

Rapamycin, which has immunosuppressant, antiinflammatory and antifungal activities, can be cleaved between the C-31 and C-32 carbons due to base degradation attributed to a reverse aldol reaction. Reduction of the ketone functionality at the C-33 position removes this pathway for decomposition. Reduction of the C-33 ketone of rapamycin gives a compound of Formula I as shown below.

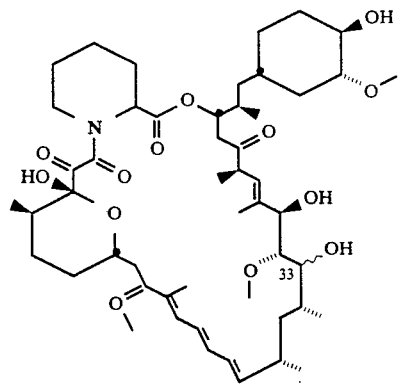

The preferred compound is that shown in part below as Formula II where the configuration of the substituents on C-33 is the R configuration.

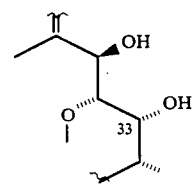

Formula I compounds display modified pharmacodynamic behavior and possess immunosuppressive and/or antifungal and/or antiinflammatory activity in vivo and/or inhibit thymocyte proliferation in vitro and are therefore useful in the treatment of transplant rejection, autoimmune disease (i.e., lupus, rheumatoid arthritis, diabetes mellitus, multiple sclerosis), *Candida albicans* infections, and diseases of inflammation.

DETAILED DESCRIPTION OF THE INVENTION

Sodium triacetoxyboroydride is reported to selectively reduce β-hydroxy ketones in an anti fashion (Evans, D. A.; Chapman, K. T.; Carreira, E. M., J. Amer. Chem. Soc. 1988, 110, 3560–3578). Thus, reduction of rapamycin with sodium triacetoxyborohydride yields the preferred 33-α-hydroxy analog or 33-deoxo-33-(R)-hydroxyrapamycin II as shown in the following equation.

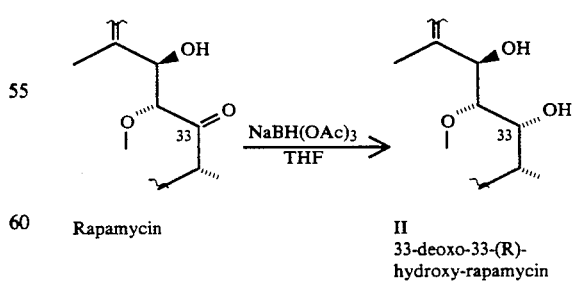

Rapamycin     II
              33-deoxo-33-(R)-
              hydroxy-rapamycin

The following experimental procedure is illustrative of the reduction reaction.

EXAMPLE 1

33-Deoxy-33-hydroxyrapamycin

A solution of rapamycin (1.05 g, 1.15 mmol) in tetrahydrofuran (40 mL) was treated with powdered sodium triacetoxyborohydride (0.52 g, 2.46 mmol) and stirred under nitrogen at room temperature for 2 h. The reaction mixture was then stored at $-20°$ C. for seven days. TLC indicated the reaction to be about 70% complete so the reaction mixture was partitioned between diethyl ether (50 mL) and 1N HCl (50 mL). The organic layer was washed with brine (50 mL), dried (MgSO$_4$), concentrated and chromatographed on silica gel (3.9×15 cm, ethyl acetate). The product fractions which contained unreacted rapamycin were combined and chromatographed by Prep HPLC (8 μm silica gel, 4.1 mm×30 cm, 1/1: THF/hexane). The clean fractions were combined and dissolved in aqueous methanol. The mixture was concentrated to effect crystallization and the power was filtered off to give 200 mg. Spectral Data follows. IR (KBr) 1680, 1730, 2920, 3430 cm.$^{-1}$, $^1$H-NMR (CDCL$_3$) δ 1.28 (3H, t, J=7.14 Hz), 1.65 (3H, s), 1.74 (3H, s), 3.14 (3H, s), 3.34 (3H, s), 3.41 (3H, s), 4.20 (2H, q, J=7.14 Hz), 4.30 (2H, dd); Mass Spec (neg. ion FAB) m/z 999 (94%), 590 (15%), 407 (16%), 379 (4%), 253 (6%), 167 (100%).

Analysis Calcd. for C$_{55}$H$_{85}$NO$_{15}$.0.5H$_2$O C, 65,45, H, 8.59, N, 1.39. Found C, 65.29, H, 8.64, N, 1.60.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the percent inhibition of lymphoproliferation of 1 μM.

$$\frac{^3H\text{-control thymus cells} - H^3\text{-rapamycin-treated thymus cells}}{^3H\text{-control thymus cells} - H^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3H\text{-}PLN \text{ cells control } C3H \text{ mouse } - \, ^3H\text{-}PLN \text{ cells rapamycin-treated } C3H \text{ mouse}}{^3H\text{-}PLN \text{ cells control } C3H \text{ mouse } - \, ^3H\text{-}PLN \text{ cells test compound-treated } C3H \text{ mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grated on the dorsum of the recipient as a homograt, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results obtained with the R-isomer of 33-deoxy-33-β-hydroxyrapamycin in the three standard test procedures.

| Compound | LAF[1] | PLN[2] | Skin Graft[3] |
|---|---|---|---|
| Rapamycin | 3.3 | 1 | 12.5 |
| Example 1 | 4.7 | 0.59 | 10.0 |

[1]IC$_{50}$ (nM)
[2]Activity relative to rapamycin
[3]Mean survival days

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC (μg/ml) to inhibit growth. The results of this test procedure showed that the compounds of this invention have antifungal activity; however, it was surprising that the preferred compound of this invention was less active than the parent compound, rapamycin.

| | Anti-Candida Activity (μg/mL)* | | | | |
|---|---|---|---|---|---|
| Compound | ATCC 10231 | ATCC 38246 | ATCC 38247 | ATCC 38248 | 3669 |
| Rapamycin | 0.03 | 0.25 | 0.03 | 0.006 | 0.25 |
| Example 1 | 0.05 | >0.4 | 0.1 | 0.2 | 0.4 |

*Minimal Inhibitory Concentration (MIC)

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

What is claimed is:

1. A compound according to the formula

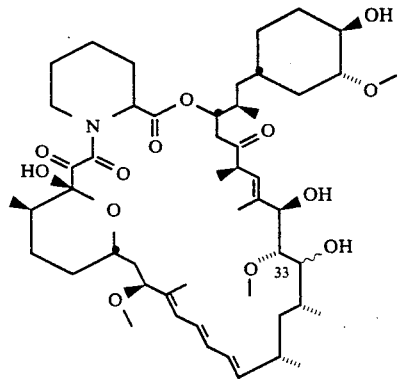

or a pharmaceutically acceptable salt thereof.

2. A compound according to claim 1 which is 33-deoxo-33-(R)-hydroxyrapamycin or a pharmaceutically acceptable salt thereof.

* * * * *